United States Patent
Jeon (10) Patent No.: US 7,450,981 B2
(45) Date of Patent: Nov. 11, 2008

(54) APPARATUS AND METHOD FOR MEASURING BLOOD COMPONENT USING LIGHT TRANS-REFLECTANCE

(75) Inventor: Kye-Jin Jeon, Suwon-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 364 days.

(21) Appl. No.: 11/206,813

(22) Filed: Aug. 19, 2005

(65) Prior Publication Data

US 2006/0100491 A1     May 11, 2006

(30) Foreign Application Priority Data

Nov. 11, 2004    (KR) ...................... 10-2004-0091849

(51) Int. Cl.
     *A61B 5/1455*      (2006.01)
(52) U.S. Cl. ........................ 600/318; 600/319; 600/322
(58) Field of Classification Search .................. 600/318, 600/319, 321, 322
See application file for complete search history.

(56) References Cited

U.S. PATENT DOCUMENTS

| | | | |
|---|---|---|---|
| 4,597,392 A | 7/1986 | Opitz et al. | |
| 5,560,356 A | 10/1996 | Peyman | |
| 6,315,955 B1 | 11/2001 | Klein | |
| 6,420,709 B1 | 7/2002 | Block et al. | |
| 6,442,409 B1 | 8/2002 | Peyman | |
| 2005/0075546 A1* | 4/2005 | Samsoondar et al. | 600/310 |

FOREIGN PATENT DOCUMENTS

| | | |
|---|---|---|
| JP | 2004-257776 | 9/2004 |
| WO | WO 02/03855 | 1/2001 |

OTHER PUBLICATIONS

Chinese Office Action issued Oct. 26, 2007 for Chinese Patent Application 2005100875536.

\* cited by examiner

*Primary Examiner*—Eric F Winakur
*Assistant Examiner*—Etsub D Berhanu
(74) *Attorney, Agent, or Firm*—Staas & Halsey LLP (57) ABSTRACT

An apparatus for measuring a blood component using the trans-reflectance of light irradiated to a transflective member disposed behind a test site. The apparatus includes an optical source unit irradiating light to the test site of a test subject; a transflective unit transflecting light transmitted through the test site; a detection unit detecting the transflected light; and an analysis unit analyzing the transflected light detected in the detection unit. A related method includes irradiating the light to the test site; transflecting light through the test site, detecting the transflected light, and analyzing the detected light. Blood component measurement can be easily performed without collecting blood by analyzing the transflected light with a high optical power containing much information about a blood component.

13 Claims, 5 Drawing Sheets

|  | MEAN PATH LENGTH (mm) | TRANSFLECTIVITY | EFFECTIVE PATH LENGTH (mm) |
|---|---|---|---|
| 320 | 0.280456 | 0.0838 | 0.163 |
| 322 | 5.416882 | 0.0558 | 2.093 |
| 324 | 5.697338 | 0.00468 | 0.185 |
| 326 | 8.686234 | 9.275E-05 | 0.00558 |
| 328 | 11.67513 | 1.837E-06 | 0.000149 |

TOTAL TRANSFLECTIVITY = 14.4%
TOTAL EFFECTIVE PATH LENGTH = 2.45mm

FIG. 4B

|  | MEAN PATH LENGTH (mm) | TRANSFLECTIVITY | EFFECTIVE PATH LENGTH (mm) |
|---|---|---|---|
| 320 | 0.146381 | 0.054875 | 0.125572 |
| 322 | 4.733856 | 0.008618 | 0.63778 |
| 324 | 4.880238 | 0.000473 | 0.03608 |
| 326 | 7.393547 | 2.41E-06 | 0.000278 |
| 328 | 9.906857 | 1.23E-08 | 1.9E-06 |

TOTAL TRANSFLECTIVITY = 6.4%
TOTAL EFFECTIVE PATH LENGTH = 0.80mm

APPARATUS AND METHOD FOR MEASURING BLOOD COMPONENT USING LIGHT TRANS-REFLECTANCE

CROSS-REFERENCE TO RELATED APPLICATIONS

This application claims priority from Korean Patent Application No. 10-2004-0091849, filed on Nov. 11, 2004, in the Korean Intellectual Property Office, the disclosure of which is incorporated herein in its entirety by reference.

BACKGROUND OF THE INVENTION

1. Field of the Invention

The present invention relates to a blood component measurement, and more particularly, to an apparatus and a method for measuring a blood component using the trans-reflectance of light irradiated to a transflective material disposed behind a test site.

2. Description of the Related Art

Diabetes is a modern lifestyle disease and currently has a prevalence of 5% of the global population, which is rising continuously. Diabetes is a chronic disease that has no perfect cure and requires lifetime self-management.

The term "self-management" indicates that a diabetic patient collects blood, performs the determination of a blood glucose level that is significantly affected by food intake, physical activity, drug or insulin therapy, and then provides the daily blood glucose determinations to a doctor to help the doctor choose a medical treatment.

However, due to pain and concern about infections by frequent blood collecting, a blood glucose test in itself increases the burden on diabetic patients. In this respect, methods of determining a glucose level in human blood by irradiating harmless light to a predetermined site of the human body and measuring the intensity of light that reacted with the human body, instead of blood-collecting, have been continuously studied.

Such studies have also been done on other blood components, in addition to blood glucose. A blood component measuring apparatus is generally classified into a reflection type and a transmission type. A reflection type blood component measuring apparatus measures a blood component in a human tissue by analyzing reflected light among incident light into the tissue. A transmission type blood component measuring apparatus measures a blood component in a human tissue by analyzing transmitted light among incident light into the tissue.

With respect to the reflection type blood component measuring apparatus, the mean path length of reflected light is very short, and thus, there arises a problem that the reflected light can hardly detect internal information of the human tissue. On the other hand, it is difficult to interface the transmission type blood component measuring apparatus with the human tissue or skin. Further, the optical power of transmitted light is too weak to measure.

SUMMARY OF THE INVENTION

Accordingly, it is an aspect of the present invention to provide an apparatus and a method for measuring a blood component using the trans-reflectance of light irradiated to a transflective material disposed behind a test site.

To achieve the foregoing and other aspects of the present invention, there is provided an apparatus for measuring a blood component using light trans-reflectance, the apparatus including: an optical source unit irradiating a predetermined wavelength light to a test site of a test subject; a transflective unit transflecting light transmitted through the test site among the light irradiated from the optical source unit; a detection unit detecting the transflected light; and an analysis unit analyzing the transflected light detected in the detection unit.

There is also provided a method of measuring the blood component using light trans-reflectance, including the steps of: irradiating a predetermined wavelength light to a test site; transflecting light transmitted through the test site; detecting the transflected light; and analyzing the detected light.

The above and other features and advantages of the present invention will become more apparent by describing in detail exemplary embodiments thereof with reference to the attached drawings in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENTS

Figure 1:
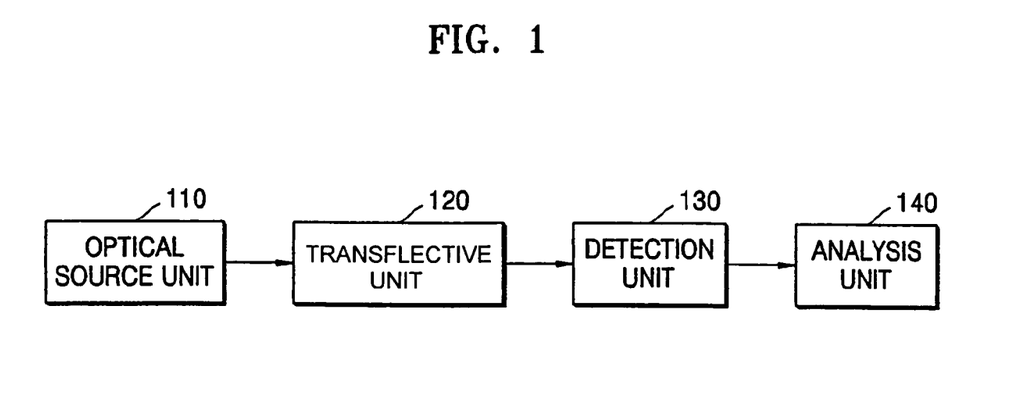
FIG. 1 is a block diagram of a blood component measuring apparatus using light trans-reflectance according to an embodiment of the present invention.

FIG. 1 is a block diagram of a blood component measuring apparatus using light trans-reflectance according to an embodiment of the present invention. Referring to FIG. 1, the blood component measuring apparatus includes an optical source unit 110, a transflective unit 120, a detection unit 130, and an analysis unit 140.

The optical source unit 110 irradiates a specific wavelength light beam onto a test site of a test subject. The optical source unit 110 may include an optical source (not shown) irradiating a specific wavelength light beam or different wavelength light beams. Preferably, the optical source includes a near-infrared lamp or a light emitting diode (LED) and the test subject is a human body. Of course, the test subject could be other mammals or animals, if desired.

Preferably, the optical source unit 110 including the optical source irradiating different wavelength light beams also includes a spectrometer (not shown). The spectrometer serves to select a specific wavelength light beam from light irradiated from the optical source.

Figure 2:
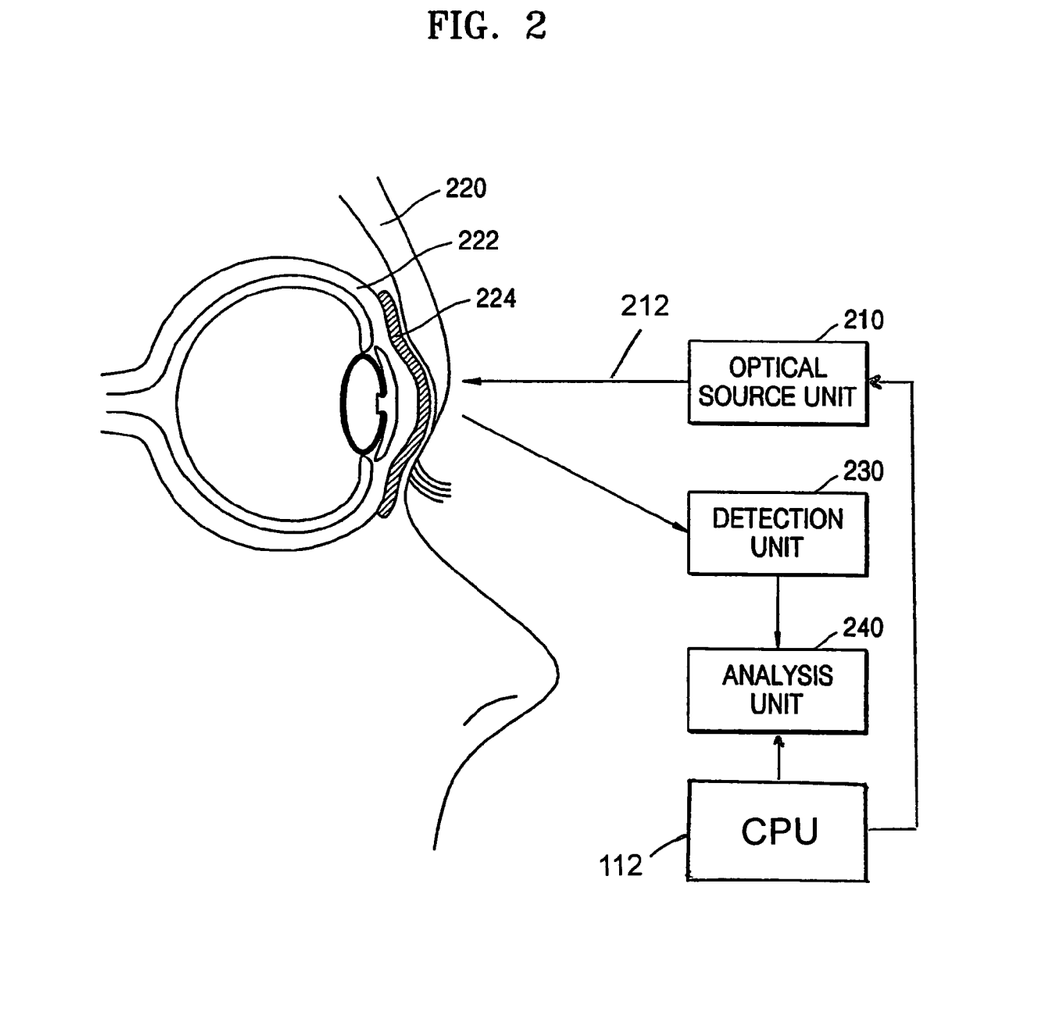
FIG. 2 is a reference view that illustrates the measurement of a blood component in an eyelid according to the present invention.

Preferably, the optical source unit 110 transfers light irradiated from the optical source to the test site via an optical fiber 212 (FIG. 2).

Examples of a blood component that can be measured by the blood component measuring apparatus include glucose, cholesterol, hemoglobin, albumin, triglyceride, alcohol and gamma (γ)-globulin.

Generally, these components can be detected in a near-infrared wavelength range of 1,600-1,800 nm or 2,100-2,350 nm. For example, glucose in blood can be measured by applying light reacting with glucose in the blood.

Preferably, the test site is a part of the human body of which the tissue and skin are thin. When a part of the human body of which the tissue and skin are thick is used as the test site, the optical power of transmitted light through the thick tissue and skin is too weak to measure. It is preferable that a test site has a tissue thickness of less than 2 mm and a skin thickness of less than 0.05 mm.

Preferably, the test site is a part of the human body in which blood vessels are congested.

The transflective unit 120 transflects light transmitted through the test site among light irradiated from the optical source unit 110. The phrase "transflective unit 120 transflects light" indicates that light transmitted through the test site is reflected back to the test site while maintaining its optical power. Light retransmitted through the test site by the transflective unit 120 is referred to as transflected light.

As used herein, the term "transflected light" comprehends light retransmitted through a subsurface region of the test site before reaching the transflective unit 120, in addition to light retransmitted through the test site by the transflective unit 120.

Preferably, the transflective unit 120 is a lens that transflects incident light. Preferably, the lens is attached to the test site, but may be spaced a predetermined distance from the test site.

To measure a blood component without collecting blood, detection of light transmitted through or reflected from a tissue can be used. Transmitted light has abundant information about a blood component due to a long mean path length but has a low optical power. Reflected light has a strong optical power and provides convenient interfacing between a measuring apparatus and a tissue. However, reflected light has less information about a blood component due to a short mean path length. In this respect, blood component measurement based on the detection of any one of transmitted light or reflected light has a limitation. Herein, the "mean path length" indicates a traveling distance of a transflected light beam in the test site. Generally, as the mean path length decreases, less abundant internal information of the test site is detected.

The blood component measuring apparatus according to the present invention includes the transflective unit 120 to measure a blood component using transflected light with all the advantages of reflected light and transmitted light. Reflected light has advantages of strong optical power of light (hereinafter, referred to as "target light") having information about a blood component and high signal-to-noise ratio. Transmitted light has an advantage that target light has abundant information about a blood component due to a long mean path length.

To create transflected light, a material for reflecting back light transmitted to the test site is required. That is, it is preferable that the optical source unit 110 for light emission is disposed on a side of the test site and the transflective unit 120 is disposed on the other side of the test site.

The detection unit 130 detects the transflected light from the test site. The analysis unit 140 analyzes the light detected in the detection unit 130 and produces an optical property curve showing information about a blood component.

For example, in the case of measuring a blood glucose using the blood component measuring apparatus of the present invention, the optical source unit 110 irradiates light reacting with glucose to a predetermined test site. Light transmitted through the test site is retransmitted through the test site by the transflective unit 120. Light retransmitted through the test site by the transflective unit 120, i.e., transflected light, is detected in the detection unit 130. The analysis unit 140 calculates a blood glucose level based on the detected transflected light.

FIG. 2 is a reference view that illustrates the measurement of a blood component in an eyelid according to the present invention. An optical source unit 210, a detection unit 230, and an analysis unit 240 of FIG. 2 are respectively operated in the same manner as the optical source unit 110, the detection unit 130, and the analysis unit 140 of FIG. 1.

Referring to FIG. 2, a transflective unit 224 is a contact lens disposed on the cornea 222. The test subject is a human body and a test site is an eyelid 220. The transflective unit 224 transflects light transmitted through the eyelid 220.

The eyelid 220 is suitable as a test site because of a tissue thickness of less than 2 mm, a skin thickness of less than 0.05 mm, and congested blood vessels. As shown in FIG. 2, the transflective unit 224 has a contact lens shape, and thus can be easily disposed on the cornea 222, thereby ensuring good interfacing with the cornea 222. Therefore, the transflective unit 224 easily interfaces with the human body without being inserted into the human body.

Even though FIG. 2 illustrates blood component measurement based on internal information of an eyelid, the present invention is not limited thereto. The blood component measuring apparatus of the present invention can also be applied to other appropriate test sites.

Figure 3:
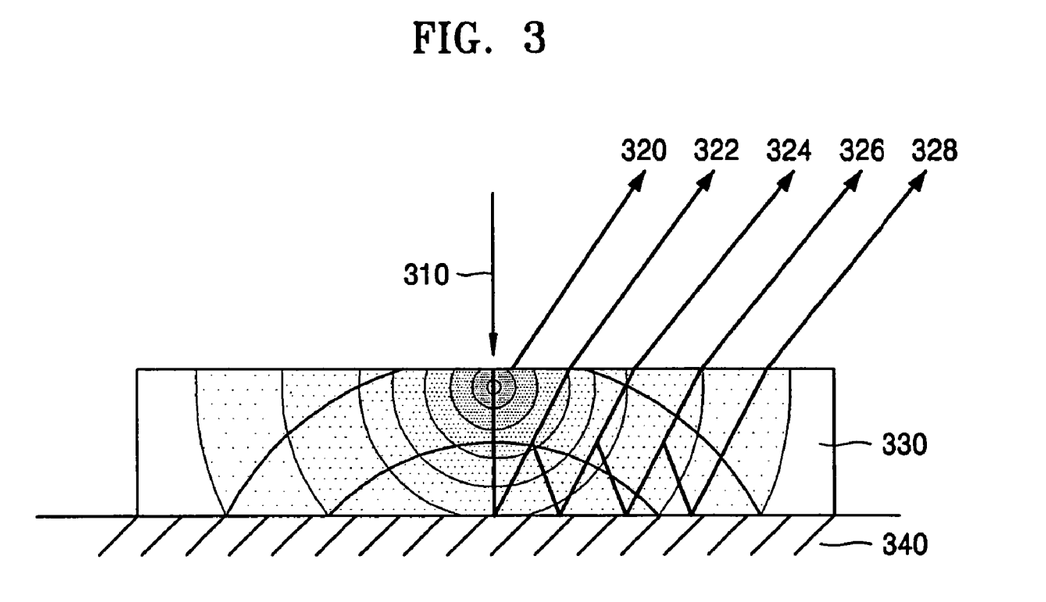
FIG. 3 is a reference view that illustrates the transflection of incident light.

FIG. 3 is a reference view that illustrates the transflection of incident light. Referring to FIG. 3, light 310 irradiated from an optical source unit (not shown) is incident in a test site 330 and then transmitted through the test site 330. A transflective unit 340 of a lens shape is stuck to a lower side of the test site 330.

Light transmitted through the test site 330 is reflected back by the transflective unit 340 and then retransmitted through the test site 330. The retransmitted light is called transflected light. FIG. 3 shows five transflected light beams 320, 322, 324, 326, and 328. The five transflected light beams are provided only for illustration convenience, and thus, the present invention is not limited thereto.

The transflected light includes a transflected light beam 320 reflected before reaching the transflective unit 340 and transflected light beams 322 through 328 reflected by the transflective unit 340.

Transflectivity (tf) indicates the ratio of the optical power of a transflected light beam (each of the transflected light beams 320 through 328) to the optical power of the incident light 310. In this respect, total transflectivity (TF) indicates the ratio of the sum of the optical powers of all the transflected light beams 320 through 328 to the optical power of the incident light 310. As transflectivity increases, more abundant information about a blood component can be acquired.

Preferably, the total transflectivity (TF) is calculated using Equation 1 below:

$$TF = R + T^2 + T^2R + T^3R^2 + T^4R^3 + \ldots, \quad (1)$$

where R is the ratio of the optical power of the transflected light beam 320 to the optical power of the incident light 310, $T^2$ is the ratio of the optical power of the transflected light beam 322 to the optical power of the incident light 310, $T^2R$ is the ratio of the optical power of the transflected light beam 324 to the optical power of the incident light 310, $T^3R^2$ is the ratio of the optical power of the transflected light beam 326 to the optical power of the incident light 310, and $T^4R^3$ is the ratio of the optical power of the transflected light beam 328 to the optical power of the incident light 310. Equation 1 has been defined considering that R represents reflectivity of tissue with constant thickness and T represents transmittance of the tissue with constant thickness.

With respect to the transflected light beam 320, little transmission through and mostly reflection from the test site 330 occurs. In this respect, the transflectivity of the transflected light beam 320 with respect to the incident light 310 can be expressed by R. The transflected light beam 322 is transmitted twice, and thus, the transflectivity of the transflected light beam 322 with respect to the incident light 310 can be expressed as $T^2$. The transflectivities of the transflected light beams 324 through 328 can be explained in the same manner as above.

Figure 4A:
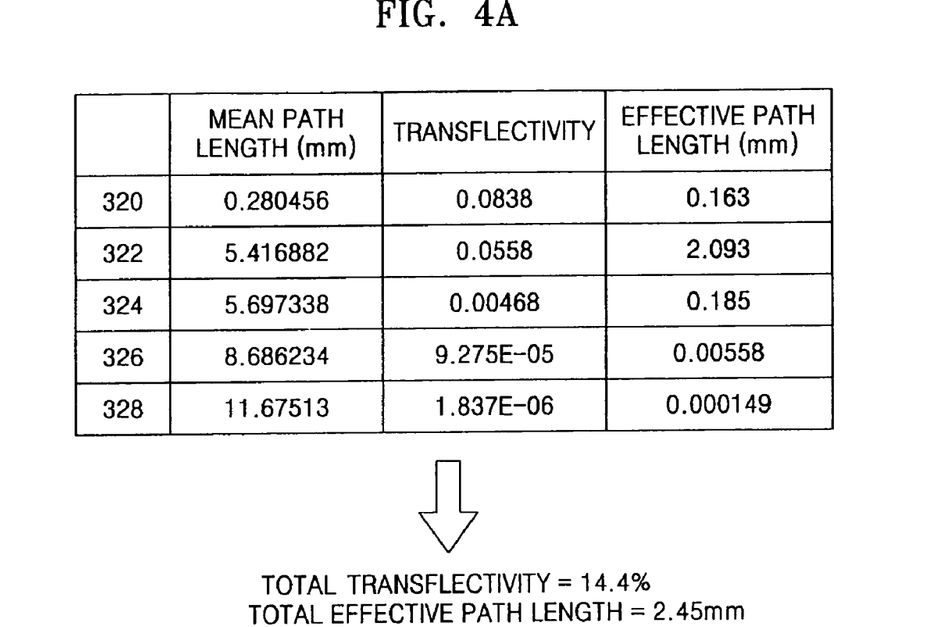
FIGS. 4A and 4B illustrate examples of total transflectivity and total effective path length.

FIG. 4A shows the total transflectivity and the total effective path length for the transflected light beams of FIG. 3 when the wavelength of light irradiated from an optical source unit is 1,600 nm.

The term "mean path length" indicates a traveling distance of a transflected light beam in the test site 330. The mean path length increases from the transflected light beam 320 to the transflected light beam 328.

Meanwhile, since the optical power of transflected light decreases from the transflected light beam 320 to the transflected light beam 328, transflectivity also decreases from the transflected light beam 320 to the transflected light beam 328. As shown in FIG. 4A, the transflected light beams 326 and 328 have negligibly low transflectivity (tf) due to their weak optical powers. In this respect, transflectivities of transflected light beams subsequent to the fifth transflected light beam are negligible for calculation of total effective path length and total transflectivity. Thus, FIG. 4A shows only the results for the five transflected light beams.

The term "effective path length" indicates a traveling distance of a transflected light beam in the test site 330 while acquiring the internal information about the test site 330. A measured value having information about a blood component is not a mean path length but an effective path length.

Meanwhile, to acquire the internal information about the test site 330 while transflected light passes through the test site 330, the optical power of the transflected light must exceed a predetermined value. Herein, the predetermined value is a value of system noise which exists in the test site always. In this respect, to calculate an effective path length, a mean path length must be multiplied by an appropriate value (weight). Preferably, the appropriate value is a value reflecting the optical power of transflected light.

As shown in FIG. 3 and FIG. 4A, when a 1,600 nm light is irradiated to the test site 330, the total transflectivity is 14.4% and the total effective path length is 2.45 mm. The total transflectivity is equal to the sum of the individual transflectivities of the transflected light beams 320 through 328. That is, the total transflectivity is given as 0.0838+0.0558+0.00468+9.275E−05+1.837E−06=0.144. The total effective path length is equal to the sum of the individual effective path lengths of the transflected light beams 320 through 328. That is, the total effective path length is given as 0.163+2.093+0.185+0.00558+0.000149=2.45.

Figure 4B:
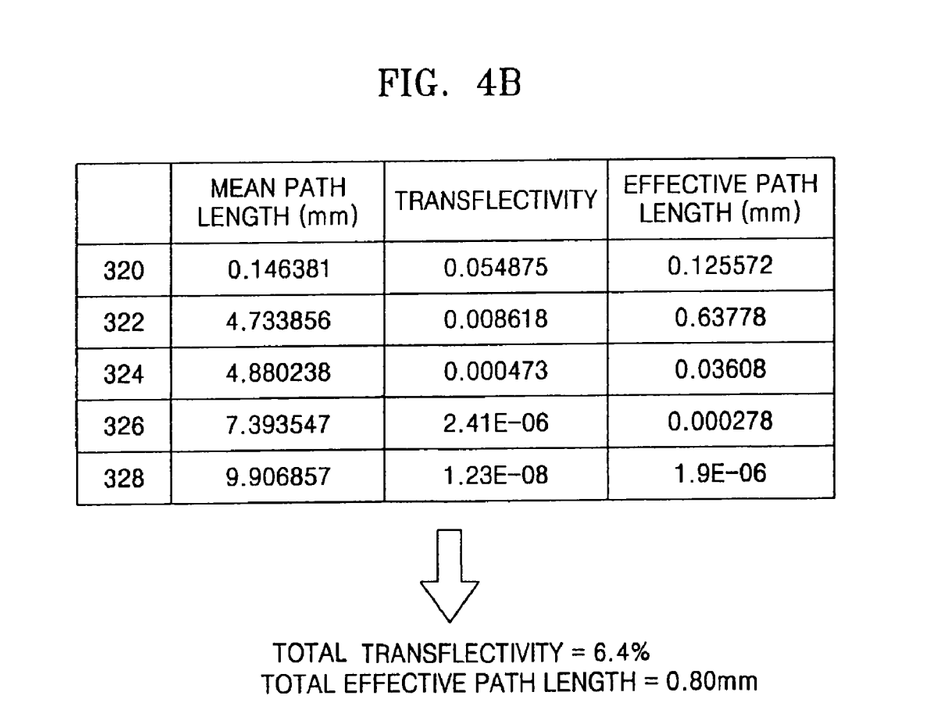

FIG. 4B shows the total transflectivity and the total effective path length for the transflected light beams of FIG. 3 when the wavelength of light irradiated from an optical source unit is 2,200 nm. The detailed description of FIG. 4A can also be applied to FIG. 4B. As shown in FIG. 4B, the total transflectivity is 6.4% and the total effective path length is 0.80 mm.

Figure 5A:
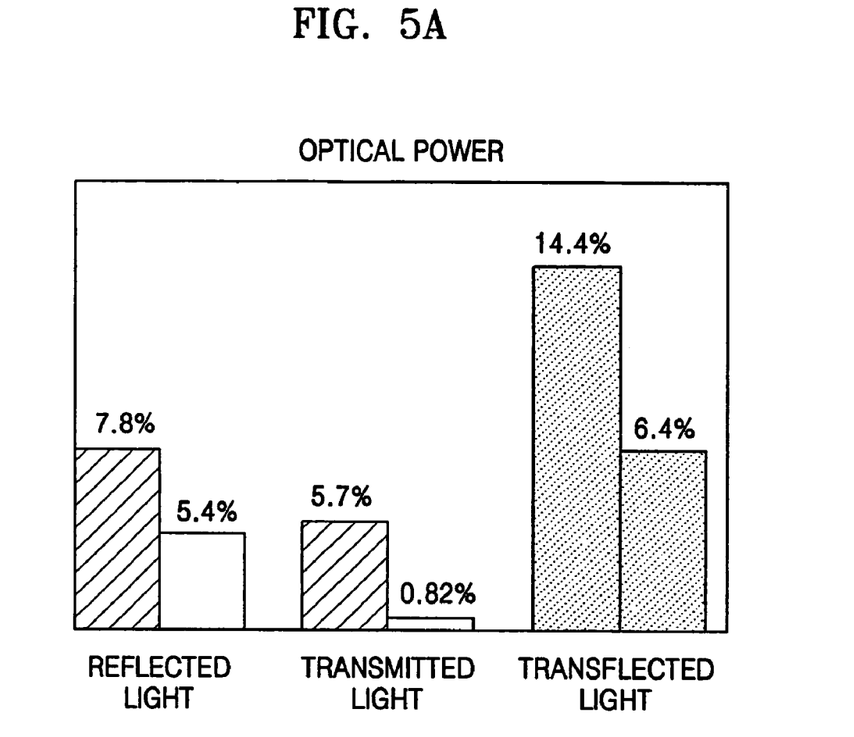
FIG. 5A is a histogram showing the total optical power for each of reflected light, transmitted light, and transflected light with respect to incident light.
Figure 5B:
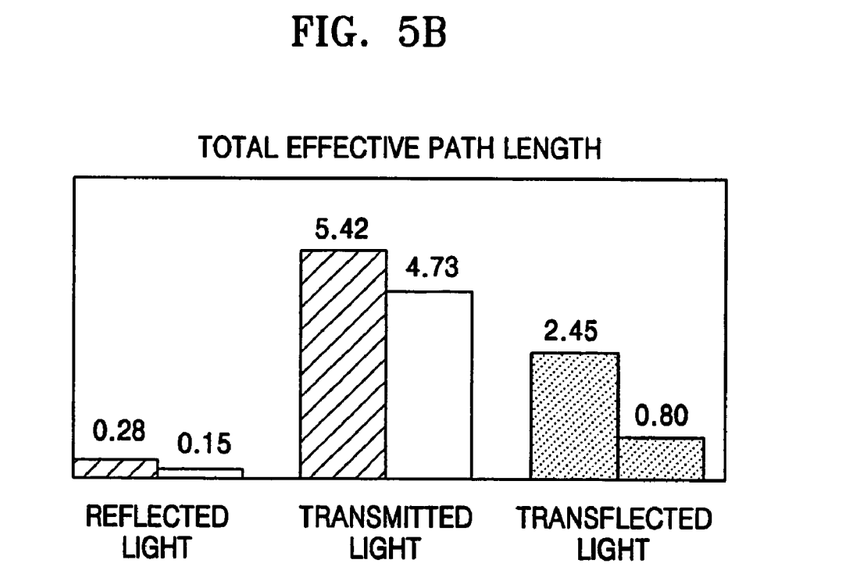
FIG. 5B is a histogram showing the total effective path length for each of reflected light, transmitted light, and transflected light with respect to incident light.

FIG. 5A is a histogram showing the optical powers for reflected light, transmitted light, and transflected light with respect to incident light, and FIG. 5B is a histogram showing the total effective path lengths for reflected light, transmitted light, and transflected light with respect to incident light.

Histograms shown in FIGS. 5A and 5B are expressed pairwise. Each left histogram shows the measured value for target light with respect to incident light with a wavelength of 1,600 nm and each right histogram shows the measured value for target light with respect to incident light with a wavelength of 2,200 nm.

As described above, to measure a blood component without collecting blood, detection of light transmitted through or reflected from a tissue can be used.

As shown in FIG. 5A, in blood component measurement using transflected light, target light has a stronger optical power, relative to blood component measurement using reflected light or transmitted light. All of reflected light, transmitted light, and transflected light have information about a blood component. However, since the optical power of the transflected light is the strongest, the transflected light can be more easily used in blood component measurement.

As shown in FIG. 5B, transmitted light has the longest effective path length. However, the optical power of the transmitted light is much weaker than that of reflected light and transflected light, as shown in FIG. 5A. In particular, the ratio of the optical power of the transmitted light to the optical power of incident light with a wavelength of 2,200 nm is as low as 0.82. In this regard, the transflected light can be more easily used in blood component measurement even though it has a shorter effective path length than the transmitted light.

Figure 6:
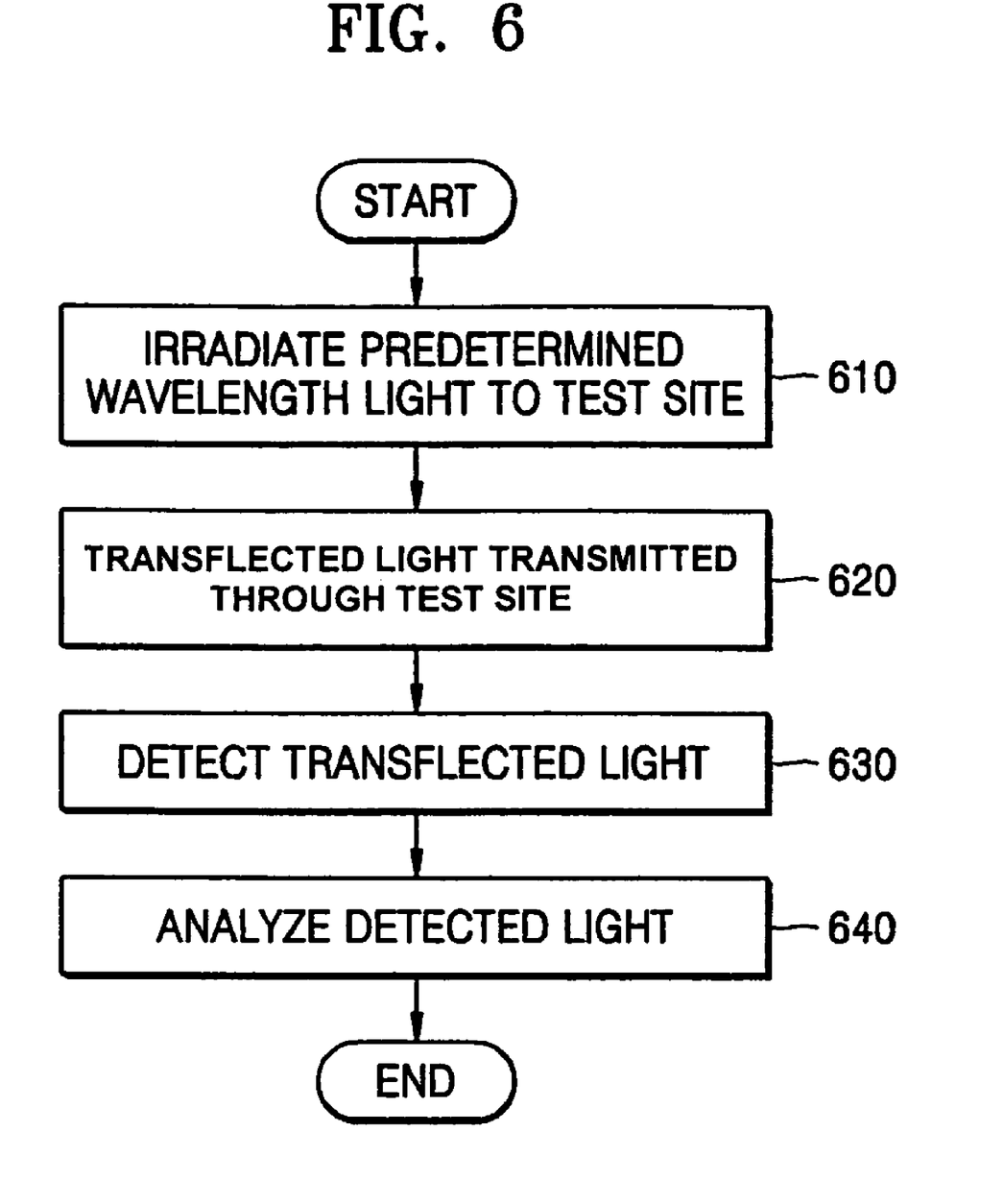
FIG. 6 is a flowchart that illustrates a blood component measuring method using light trans-reflectance according to an embodiment of the present invention.

FIG. 6 is a flowchart that illustrates a blood component measuring method using light trans-reflectance according to an embodiment of the present invention. The blood component measuring method of FIG. 6 will now be described in detail with reference to the blood component measuring apparatus of FIG. 1.

Referring to FIG. 6, the optical source unit 110 irradiates a specific wavelength light (operation 610). Light irradiated from the optical source unit 110 is incident to a test site and then transmitted through the test site. The transflective unit 120 reflects light transmitted to the test site back through the test site (operation 620).

The transflected light is retransmitted through the test site. The detection unit 130 detects the transflected light (operation 630). The analysis unit 140 analyzes the results detected in the detection unit 130 (operation 640).

The present invention also includes automating the above-described method using a computer 112, such as a CPU, shown in FIG. 2. The detection unit 230 and/or the analysis unit 240 can be separate from the computer 112 or a part thereof. In this regard, the computer includes a computer program for controlling the optical source unit 110, the detection unit 130 and the analysis unit 140 to measure, e.g., a blood component such as glucose when irradiated light is transflected by the transflective unit 120.

As apparent from the above description, according to a blood component measuring apparatus and method using light trans-reflectance of the present invention, transflected light with a high optical power containing much information about a blood component is analyzed. Therefore, blood component measurement can be easily performed without collecting blood.

Furthermore, a blood component measuring apparatus and method using light trans-reflectance according to the present invention eliminates a test subject's usual dislike or discomfort arising from conventional blood component tests.

While the present invention has been particularly shown and described with reference to exemplary embodiments of a blood component measuring apparatus and method using light trans-reflectance, it will be understood by those skilled in the art that the foregoing is illustrative only of the principles of the invention. Since numerous modifications and changes will readily occur to those skilled in the art, it is not desired to limit the invention to the exact construction and operation shown and described. Accordingly, all suitable modification and equivalents may be resorted to that fall within the scope of the invention and the appended claims.

What is claimed is:

1. An apparatus for measuring a blood component using light trans-reflectance, the apparatus comprising:
    an optical source unit to irradiate light to a test site of a test subject;
    a transflective unit to transflect light transmitted through the test site among the light irradiated from the optical source unit;
    a detection unit to detect the transflected light; and
    an analysis unit to analyze the transflected light detected in the detection unit,
    wherein the test subject is a human body and the test site is an eyelid, and
    wherein the transflective unit is a contact lens configured to transflect light transmitted through the eyelid.

2. The apparatus of claim 1, wherein the optical source unit includes an optical source that irradiates a 1,600-1,800 nm or 2,100-2350 nm wavelength light beam.

3. The apparatus of claim 1, wherein the optical source unit includes an optical source that irradiates different wavelength light beams, and a spectrometer to select a specific wavelength light beam from the different wavelength light beams.

4. The apparatus of claim 1, wherein the optical source unit irradiates near-infrared light to the test site.

5. The apparatus of claim 1, wherein the transflecting light is infrared light which is in the ranges of 1600-1800 nm or 2100-2350 nm.

6. The apparatus of claim 1, wherein the optical source unit irradiates light reacting with glucose to the test site.

7. The apparatus of claim 1, wherein the optical source unit includes an optical fiber to transmit light from the optical source unit to the test site.

8. The apparatus of claim 1, wherein the transflective unit is a contact lens transflecting light irradiated from the optical source unit and the contact lens is adapted to be attached to the test site.

9. The apparatus of claim 1, wherein the contact lens is adapted to be disposed on the cornea.

10. The apparatus of claim 1, wherein the blood component is selected from the group consisting of glucose, cholesterol, hemoglobin, albumin, triglyceride, alcohol and gamma globulin.

11. The apparatus of claim 1, wherein the transflective unit is configured to be spaced from a cornea.

12. A method of measuring a blood component using light trans-reflectance, the method comprising:
    irradiating light to a test site;
    transflecting light transmitted through the test site among the light irradiated to the test site;
    detecting the transflecting light; and
    analyzing the detected light by calculating a blood component level based on the transflected light,
    wherein the operation of irradiating the light to the test site includes irradiating light reacting with the blood component to an eyelid, and
    wherein the operation of transflecting the light transmitted through the test site includes transflecting light transmitted through the eyelid.

13. The method of claim 12, wherein the blood component is glucose and the operation of analyzing the light includes calculating a glucose level in the blood based on the transflecting light.

* * * * *

UNITED STATES PATENT AND TRADEMARK OFFICE
CERTIFICATE OF CORRECTION

PATENT NO. : 7,450,981 B2
APPLICATION NO. : 11/206813
DATED : November 11, 2008
INVENTOR(S) : Kye-jin Jeon It is certified that error appears in the above-identified patent and that said Letters Patent is hereby corrected as shown below:

Column 8, Line 3, change "transflecting" to --transflected--.

Column 8, Line 28, change "transflecting" to --transflected--.

Column 8, Lines 39-40, change "transflecting" to --transflected--.

Signed and Sealed this

Seventeenth Day of February, 2009

JOHN DOLL
*Acting Director of the United States Patent and Trademark Office*